Oct. 30, 1962 D. H. MOREY, JR Plant Pat. 2,188
ROSE PLANT
Filed Nov. 15, 1961
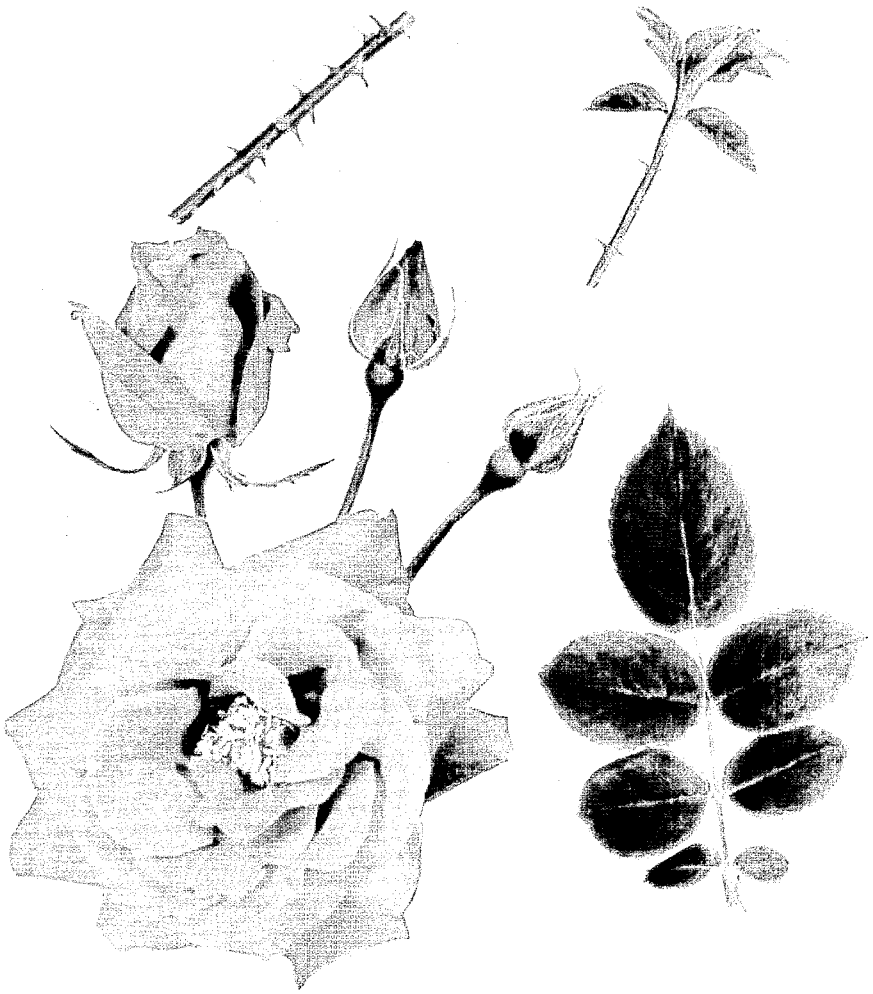
Inventor.
Dennison H. Morey, Jr.
By: Robb & Robb
Attorneys.

United States Patent Office

Plant Pat. 2,188
Patented Oct. 30, 1962

2,188
ROSE PLANT

Dennison H. Morey, Jr., Pleasanton, Calif., assignor to Jackson & Perkins Company, Newark, N.Y., a corporation of New York Filed Nov. 15, 1961, Ser. No. 152,697
1 Claim. (Cl. 47—61)

The present invention relates to a new and distinct variety of rose plant of the hybrid tea class, which was originated by me by crossing the variety "Mardi Gras" (Plant Patent No. 1,139) with the variety "Chrysler Imperial" (Plant Patent No. 1,167).

The primary objective of this breeding was to produce a new rose variety of the hybrid tea class in which there is combined the red flower color of the parent variety "Mardi Gras" and the flower fragrance of the parent variety "Chrysler Imperial." This objective was fully achieved, along with other desirable improvements, as evidenced by the following unique combination of characteristics which are outstanding in the new variety and which distinguish it from its parents, as well as from all other varieties of which I am aware:

(1) A bushy and well-clothed plant habit;
(2) A profuse blooming habit;
(3) A high-centered flower form;
(4) A very fragrant, clean, fresh tea flower scent; and
(5) An attractive red flower color corresponding to Spectrum Red, lightly overcast with Scarlet-Red.

Asexual reproduction of my new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Mardi Gras."
*Pollen parent.*—"Chrysler Imperial."

Classification:
*Botanic.*—Hybrid tea.
*Commercial.*—Hybrid tea.

*Flower*

(Observations made from specimens grown outdoors at Newark, New York, during the early morning about mid-August.)

Blooming habit: Recurrent—continuous.

Bud:
*Size.*—Large.
*Form.*—Urn; is not affected by wet or hot weather.
*Color.*—When sepals first divide—Carmine, Plate 1. When petals begin to unfurl—Carmine, Plate 1, very lightly overcast with Spectrum Red, Plate 1 on the outer edges of the petals. When half-blown: inside of petals—Spectrum Red, Plate 1, very lightly overcast with Carmine, Plate 1; reverse of petals—Spectrum Red, Plate 1.
*Sepals.*—Slightly branched; curl back when petals begin to unfurl. Color: inside—Turtle Green, Plate 32; outside—Rinnemann's Green, Plate 18.
*Calyx.*—Color—Spinach Green, Plate 5. Shape—apple. Size — small. Aspect — smooth. Odor when rubbed—none.
*Peduncle.* — Length — medium. Aspect — rough. Strength—erect; slender. Color—Spinach Green, Plate 5.
*Opening.*—Opens up well; is not affected by adverse weather conditions.

Bloom:
*Size.*—Large. Average size when fully expanded—from 5 inches to 5½ inches.
*Borne.*—Singly.
*Stems.*—Long; strong.
*Form (when first open).*—High-centered. Permanence—retains its form to the end, but outer petals curl back.
*Petalage.*—Double (full but open center). Number of petals under normal conditions—35.
*Color.*—Center of flower—Scarlet-Red, Plate 1, lightly overcast with Carmine, Plate 1. Outer petals—Scarlet-Red, Plate 1. Base of petals (aiglet)—Light Cadmium, Plate 4. Inside of petals—Spectrum Red, Plate 1, lightly overcast with Scarlet Red, Plate 1. Reverse of petals—Carmine, Plate 1, lightly overcast with Rose Red, Plate 12. General tonality from a distance—Spectrum Red, Plate 1, lightly overcast with Scarlet-Red, Plate 1.
*Discoloration.*—General tonality at end of first day—Scarlet-Red, Plate 1, lightly overcast with Carmine, Plate 1. Second day—Spectrum Red, Plate 1, lightly overcast with Scarlet-Red, Plate 1. Third day—Spectrum Red, Plate 1, overcast with Scarlet Red, Plate 1.

Petals:
*Texture.*—Leathery; is not affected by wet or hot weather.
*Appearance.*—Inside—velvety. Outside—satiny.
*Form.*—Oval; slightly notched.
*Arrangement.*—Imbricated (regularly arranged shingle-like).
*Petaloids in center.*—Few; large.
*Persistence.*—Drop off cleanly.
*Fragrance.* — Strong. Nature — clean, fresh tea scent.
*Lasting quality.*—On the plant—long. As cut flower—long.

*Genital Organs*

Stamens, anthers: Large; many; regularly arranged around styles. Color—Apricot Yellow, Plate 4.
Stamens, filaments (threads): Medium length. Color—Deep Chrome, Plate 3.
Pollen: Color—Maize Yellow, Plate 4.
Styles: Bunched; uneven length; medium length; thin.
Stigmas: Color—Barium Yellow, Plate 16.
Ovaries: All enclosed in calyx.
Hips: None.
Seeds: None.

*Plant*

Form: Bush.
Growth: Vigorous; upright; bushy.
Foliage: Compound of 5–7 leaflets.
*Size.*—Large.
*Quantity.*—Abundant.
*Color.*—New foliage: upper side—Oil Green, Plate 5, lightly overcast with Oxblood Red, Plate 1; under side—Yellowish Oil Green, Plate 5, overcast with Carmine, Plate 1. Old foliage: upper side—Forest Green, Plate 17; under side—Light Elm Green, Plate 17.
*Shape.*—Oval pointed.
*Texture.*—Upper side — leathery. Under side—smooth.

*Ribs and veins.*—Ordinary.
*Edge.*—Serrated (saw-toothed).
*Serration.*—Single; small.
*Leaf stem.*—Color—Biscay Green, Plate 17. Under side—prickly.
*Stipules.*—Medium length; smooth.

Wood:

*New wood.*—Color.—Light Bice Green, Plate 17. Bark—smooth.
*Old wood.*—Color—Forest Green, Plate 17. Bark—smooth.

Thorns:

*Thorns.*—Quantity: on main stalks from base—ordinary; on laterals from stalk—ordinary. Form—narrow base; medium length; hooked downward. Color (when young)—Begonia Rose, Plate 1.

Position—irregular.
*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by the unique combination of a bushy and well-clothed plant habit, a profuse blooming habit, a high-centered flower form, a very fragrant, clean, fresh tea flower scent, and an attractive red flower color corresponding to Spectrum Red lightly overcast with Scarlet-Red.

No references cited.